(12) United States Patent (10) Patent No.: US 7,897,626 B2
Bothe et al. (45) Date of Patent: Mar. 1, 2011

(54) 2-SUBSTITUTED THIAZOLE-4-CARBOXAMIDE DERIVATIVES, THEIR PREPARATION AND USE AS PHARMACEUTICALS

(75) Inventors: Ulrich Bothe, Berlin (DE); Arne Von Bonin, Glienicke-Nordbahn (DE); Duy Nguyen, Berlin (DE); Ulf Bömer, Glienicke (DE); Judith Guenther, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 0 days.

(21) Appl. No.: 12/330,696

(22) Filed: Dec. 9, 2008

(65) Prior Publication Data

US 2009/0149517 A1 Jun. 11, 2009

Related U.S. Application Data

(60) Provisional application No. 61/022,671, filed on Jan. 22, 2008.

(30) Foreign Application Priority Data

Dec. 10, 2007 (EP) .................................. 07076070

(51) Int. Cl.
*A61K 31/4155* (2006.01)
*A61K 31/426* (2006.01)
*C07D 277/24* (2006.01)

(52) U.S. Cl. ......................... 514/365; 548/200
(58) Field of Classification Search .................. None
See application file for complete search history.

(56) References Cited

FOREIGN PATENT DOCUMENTS

| EP | 1 832 586 A1 | | 9/2007 |
|---|---|---|---|
| WO | WO 2004/058750 | * | 7/2004 |
| WO | WO 2008/054702 A1 | | 5/2008 |

OTHER PUBLICATIONS

S. Naik, G. Bhattacharjya, B. Talukdar, B. K. Patel, Eur. J. Org. Chem., 2004, 1254-1260.*
Golub et al. "Molecular Classification of Cancer: Class Discovery and Class Prediction by Gene Expression Monitoring." Science (1999), vol. 286, 521-537.*
Huff, Joel R. HIV Protease: A novel chemotherapeutic target for AIDS. Journal of Medicinal Chemistry, 34(8) (1991), 2305-2314.*
Lala et al. "Role of nitric oxide in tumor progression: Lessons from experimental tumors." Cancer and Metastasis Reviews (1998), 17(1), 91-106.*
International Search Report of PCT/EP2008/010105 (Mar. 18, 2009).
XP-002487587-Online Database Chemcats Chemical Abstracts, "Aurora Screening Library", (Sep. 6, 2007).

* cited by examiner

*Primary Examiner* — Rebecca L Anderson
*Assistant Examiner* — Alicia L Otton
(74) *Attorney, Agent, or Firm* — Millen, White, Zelano & Branigan, P.C.

(57) ABSTRACT

The present invention relates to 2-substituted thiazole-4-carboxamide derivatives of the formula (I), the use thereof as medicament for the treatment of various disorders, and processes for the preparation thereof

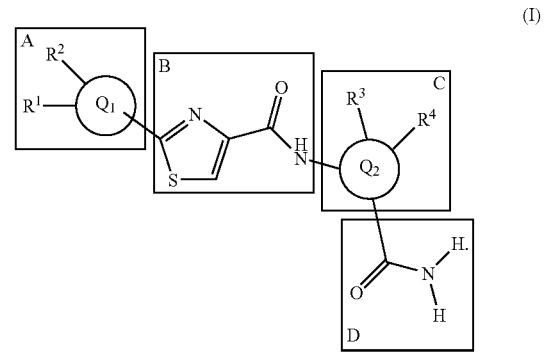

10 Claims, No Drawings

2-SUBSTITUTED THIAZOLE-4-CARBOXAMIDE DERIVATIVES, THEIR PREPARATION AND USE AS PHARMACEUTICALS

This application claims the benefit of the filing date of U.S. Provisional Application Ser. No. 61/022,671 filed Jan. 22, 2008.

The present invention relates to 2-substituted thiazole-4-carboxamide derivatives and their use as medicaments for the treatment of various disorders.

BIOLOGICAL BACKGROUND

An overreacting immune system is partly responsible for numerous chronic inflammatory disorders such as, for example, rheumatoid arthritis, Crohn's disease, asthma and multiple sclerosis. An increased release of proinflammatory cytokines leads to damage to endogenous tissue structures. The interplay of the innate and adaptive immune system is of central importance in this connection (Akira et al., 2001). Modulation of the immune system with substances which interfere with the activation of cells of the innate and/or of the adaptive immune system has antiinflammatory effects and can thus alleviate the pathological phenotype in the above disorders mentioned by way of example.

Innate immunity is based on the fact that microorganisms such as bacteria and viruses have certain inherent features via which they are recognized by the immune system and subsequently activate the latter. Certain pathogen-associated patterns ("pathogen associated molecular pattern, PAMPS") are recognized. PAMPs are recognized by the pattern recognition receptors (PRR), which include Toll-like receptors (TLR) (Janeway and Medzhitov, 2002). TLRs are homologues of the drosophila receptor protein "toll". There are ten different human TLRs. TLR one and six are coreceptors for TLR2. TLR2 recognizes inter alia lipoproteins and lipopeptides. TLR3 recognizes double-stranded RNA. TLR4 recognizes inter alia LPS of gram-negative and lipoteichoic acid of gram-positive bacteria. TLR5 recognizes flagellin, TLR9 recognizes CpG motifs in bacterial DNA (O'Neill, 2006). Coreceptors may further alter the recognition abilities of TLRs (Jiang et al., 2005).

IL-1/-18, TLR Signal Transduction

TLRs are used in signal transduction with IL-1/IL-18 cytokine receptors. IL-1 (endogenous pyrogen) greatly stimulates inflammation and induces fever. Members of the IL-1R/TLR superfamily have a TIR domain (Toll/IL1 receptor). The TIR domain is about 200 amino acids long and comprises three conserved sequence motifs. Proteins having TIR domains bind via a protein-protein interaction (O'Neill et al., 2005). Subclass one (IL-1R family) comprises three Ig-like domains, and the receptor is a heterodimer. Included therein are IL-1 receptors one and two, the coreceptor IL-1RAcP and the corresponding proteins of the IL-18 system. Subclass two (TLR family) comprises leucine-rich motifs. Toll-like receptors form homo- or heterodimers.

Activation of the TLR or IL-1, -18 receptors by the appropriate ligands initiates a multistage signal cascade. The TLR or IL-1/-18 receptor complex interacts via TIR/TIR contacts with the adaptor protein MyD88. The IL-1 associated receptor kinase (IRAK-1) normally has Tollip (Toll interacting protein) bound, which probably acts as an attenuating molecule ("silencer"). IRAK/Tollip binds to the active TLR/IL-1R complex. MyD88 displaces Tollip, thus activating IRAK1 and IRAK-4, most probably as dimer by transphosphorylation. Active IRAK leaves the receptor and binds in the cytoplasm to the adaptor molecule TRAF (Barton and Medzhitov, 2003). Further proteins are ubiquitinylated via TRAF. Ub-TRAF leads, by an unknown mechanism, to autophosphorylation of the S/T kinase TAK1 (an MAP kinase kinasekinase). TAK1 phosphorylates IκB (NF-κB activation) and MKK6. The latter is responsible for activating the MAP kinases p38 and JNK. NF-κB has been identified as nuclear factor for expression of the light antibody chain kappa in B cells, but is likewise involved in regulating many other genes. NF-κB is retained in the inactive state in the cytoplasm, where it is bound to the inhibitor IκB (Deng et al., 2000). Phosphorylation of IκB leads to proteolytic degradation of the inhibitor IκB, and the transcription factor is able to migrate into the nucleus. NF-κB is a heterodimer composed of the subunits p65 (Rel) and p50 (Bäuerle and Henkel, 1994). There are several members of this family which are able to interact in various ways. NF-κB alone cannot induce transcription. Transcriptional coactivators are necessary for gene activation, such as, for instance, p300 or CBT (Akira and Takeda, 2004).

Activation of receptors containing TIR domains is followed inter alia by release of inflammatory cytokines such as, for example, IL-1, IL-6, IL-23 and TNF-alpha (Adachi et al., 1998).

The structures of the following patent applications form the structurally close prior art:

WO2007/016292 describes N-aryl-2-arylthiazole-4-carboxamide derivatives as biofilm modulators (modulators of bacterial films) which differ because of the bicyclic C-D ring system from the compounds claimed herein.

WO2007/035478 discloses compounds which have a carboxyl group in the ortho position instead of a carboxamide group.

U.S. Pat. No. 6,274,738 describes N-aryl-2-pyridylthiazole-4-carboxamide derivatives as compounds which modulate DNA primase. However, these compounds cannot have an aminocarbonyl group on the N-aryl group in the ortho position relative to the pyridylthiazole-4-carboxamide unit. In addition, U.S. Pat. No. 4,879,295 discloses N-tetrazolylthiazolecarboxamides. Thiazolamide derivatives are mentioned in WO2006/122011 as inhibitors of viral replication. WO2005/048953 describes thiazolamide derivatives linked to an isoxazole unit as kinase inhibitors. The structures differ from the structures of the present invention, however.

The compounds disclosed in WO2007/052882 also do not have an aminocarbonyl group in the ortho position relative to the aminocarbonyl-thiazole group. A particular feature of the compounds described in WO2004072025 is, in contrast to the structures disclosed herein, a pyrrolidine ring which is additionally linked to a further substituent (such as, for example, a dimethylamino group) via a nitrogen atom.

WO200512256, WO200677424, WO2006077425 and WO200677428 disclose pyrazole derivatives as kinase inhibitors. Among the structures described are some in which a thiazolamide is linked to the pyrazole unit, although none of the pyrazole nitrogen atoms is in methylated form, and the pyrazole unit is not substituted by an aminocarbonyl group ($C(O)NH_2$) either.

Pyrazolamides which are, however, simultaneously linked to a urea unit are described in WO2005/37797.

WO2005/115986 claims pyridinamides, but in this case no linkages to sulphur-containing heterocycles such as thiazole are envisaged.

Structurally different from the compounds described herein are also the pyridinamides described in WO2005/049604 because of the linkage to an oxygen-substituted phenyl ring.

EP1666455 describes amides with an additional carboxamide structure, it not being possible for the substituent R1 to be an aminocarbonyl group.

Starting from this prior art, the object of the present invention is to provide further structures for therapy, in particular for immunomodulation.

The object is achieved by compounds of the general formula (I) with building blocks A, B, C and D,

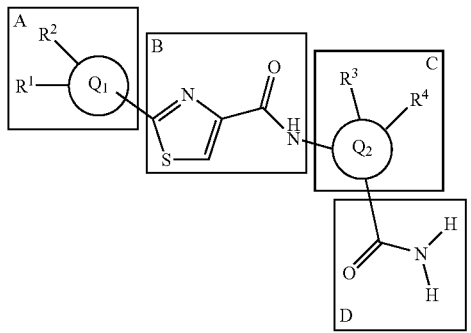

(I)

in which
the building blocks B and D are in ortho position relative to one another, and
$Q_1$ is a heteroaryl ring having 5 ring atoms,
$R^1$ and $R^2$ are independently of one another
 (i) hydrogen, hydroxy, nitro, halogen, cyano, —$CF_3$, —$NR^5R^6$ or
 (ii) —C(O)—$R^{10}$, —C(O)—$R^7$, —C(O)—$C_1$-$C_3$-fluoroalkyl, —C(O)—$NR^5R^6$, —NH—C(O)—$R^7$ or
 (iii) a $C_1$-$C_6$-alkyl, $C_2$-$C_6$-alkenyl, $C_2$-$C_6$-alkynyl, $C_1$-$C_6$-alkoxy, $C_1$-$C_6$-fluoroalkyl or a $C_1$-$C_6$-fluoroalkoxy radical,
   in each case optionally substituted one or more times, identically or differently, by $C_1$-$C_3$-alkoxy, hydroxy, —C(O)—$R^{10}$ or —$NR^8R^9$, or
 (iv) —O—$SO_2$—$NR^5R^6$, —$SO_2$—$R^7$, —$SO_2$—$NR^5R^6$,
$Q_2$ is an aryl, heteroaryl or a hydrogenated bicyclic heteroaryl ring;
$R^3$ and $R^4$ are independently of one another
 (i) hydrogen, halogen or —$NR^{11}R^{12}$, or
 (ii) a $C_1$-$C_6$-alkyl or $C_1$-$C_6$-alkoxy radical which are in each case optionally substituted one or more times, identically or differently, by hydroxy, $C_1$-$C_3$-alkoxy, —$NR^8R^9$ or heterocyclyl, where the heterocyclyl ring may be substituted one or more times, identically or differently, by $C_1$-$C_3$-alkyl or —C(O)—$R^7$, where
$R^5$ and $R^6$ are independently of one another hydrogen or a $C_1$-$C_6$-alkyl radical which is optionally substituted one or more times, identically or differently, by hydroxy, —$C_1$-$C_3$-alkoxy, —$NR^8R^9$ or heterocyclyl, where the heterocyclyl ring may be substituted one or more times, identically or differently, by $C_1$-$C_3$-alkyl or —C(O)—$R^7$, or
$R^5$ and $R^6$ form alternatively together with the nitrogen atom a 5- to 7-membered ring which optionally comprises a further heteroatom in addition to the nitrogen atom, and which is optionally substituted one or more times, identically or differently, by $C_1$-$C_6$-alkyl and/or by —C(O)—$R^7$, and
$R^7$ is a $C_1$-$C_6$-alkyl radical, and
$R^8$, $R^9$, $R^{10}$ are independently of one another hydrogen or a $C_1$-$C_6$-alkyl radical, and $R^{11}$ and $R^{12}$ are independently of one another hydrogen or a $C_1$-$C_6$-alkyl radical which is optionally substituted one or more times, identically or differently, by hydroxy, —$C_1$-$C_3$-alkoxy, —$NR^8R^9$ or heterocyclyl, where the heterocyclyl ring may be substituted one or more times, identically or differently, by $C_1$-$C_3$-alkyl or —C(O)—$R^7$, or and the salts, enantiomers and diastereomers thereof.

The invention is based on the following definitions:

$C_n$-Alkyl:

Monovalent, straight-chain or branched, saturated hydrocarbon radical having n carbon atoms.

A $C_1$-$C_6$-alkyl radical includes inter alia for example:
methyl-, ethyl-, propyl-, butyl-, pentyl-, hexyl-, iso-propyl-, iso-butyl-, sec-butyl-, tert-butyl-, iso-pentyl-, 2-methylbutyl-, 1-methylbutyl-, 1-ethylpropyl-, 1,2-dimethylpropyl-, neo-pentyl-, 1,1-dimethylpropyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-1,2-dimethylbutyl-.

A methyl, ethyl, propyl or isopropyl radical is preferred.

$C_n$-Fluoroalkyl:

Monovalent, straight-chain or branched, saturated, completely or partly fluorinated, hydrocarbon radical having n carbon atoms.

A $C_1$-$C_6$-fluoroalkyl radical includes inter alia for example:
trifluoromethyl, difluoromethyl, monofluoromethyl, pentafluoroethyl, heptafluoropropyl, 2,2,2-trifluoroethyl, 3,3,3-trifluoropropyl, 5,5,6,6,6-pentafluorohexyl, pentafluoroallyl, 1,1,1,3,3,3-hexafluoro-2-propyl A trifluoromethyl, 2,2,2-trifluoroethyl and pentafluoroethyl radical is preferred.

$C_n$-Alkenyl:

monovalent, straight-chain or branched hydrocarbon radical having n carbon atoms and at least one double bond.

A $C_2$-$C_6$ alkenyl radical includes inter alia for example:
vinyl-, allyl-, (E)-2-methylvinyl-, (Z)-2-methylvinyl-, homoallyl-, (E)-but-2-enyl-, (Z)-but-2-enyl-, (E)-but-1-enyl-, (Z)-but-1-enyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl, isopropenyl-, 2-methylprop-2-enyl-, 1-methylprop-2-enyl-, 2-methylprop-1-enyl-, (E)-1-methylprop-1-enyl-, (Z)-1-methylprop-1-enyl-, 3-methylbut-3-enyl-, 2-methylbut-3-enyl-, 1-methylbut-3-enyl, 3-methylbut-2-enyl-, (E)-2-methylbut-2-enyl-, (Z)-2-methylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1-enyl-, (Z)-1-methylbut-1-enyl-, 1,1-dimethylprop-2-enyl-, 1-ethylprop-1-enyl-, 1-propylvinyl-, 1-isopropyl-vinyl-, 4-methylpent-4-enyl-, 3-methylpent-4-enyl-, 2-methylpent-4-enyl-, 1-methylpent-4-enyl-, 4-methylpent-3-enyl-, (E)-3-methylpent-3-enyl-, (Z)-3-methylpent-3-enyl-, (E)-2-methylpent-3-enyl-, (Z)-2-methylpent-3-enyl-, (E)-1-methylpent-3-enyl-, (Z)-1-methylpent-3-enyl-, (E)-4-methylpent-2-enyl-, (Z)-4-methylpent-2-enyl-, (E)-3-methylpent-2-enyl-, (Z)-3-methylpent-2-enyl-, (E)-2-methylpent-2-enyl-, (Z)-2-methylpent-2-enyl-, (E)-1-methylpent-2-enyl-, (Z)-1-methylpent-2-enyl-, (E)-4-methylpent-1-enyl-, (Z)-4-methylpent-1-enyl-, (E)-3-methylpent-1-enyl-, (Z)-3-methylpent-1-enyl-, (E)-2-methylpent-1-enyl-, (Z)-2-methylpent-1-enyl-, (E)-1-methylpent-1-enyl-, (Z)-1-methylpent-1-enyl-, 3-ethylbut-3-enyl-, 3-ethylbut-3-enyl-, 1-ethylbut-3-enyl-, (E)-3-ethylbut-2- enyl-, (Z)-3-ethylbut-2-enyl-, (E)-2-ethylbut-2-enyl-, (Z)-2-ethylbut-2-enyl-, (E)-1-ethylbut-2-enyl-, (Z)-1-ethylbut-2-enyl-, (E)-3-ethylbut-1-enyl-, (Z)-3-ethylbut-1-enyl, 2-ethylbut-1-enyl-, (E)-1-ethylbut-1-enyl-, (Z)-1-ethylbut-1-enyl-, 2-propylprop-2-enyl-, 1-propylprop-2-enyl-, 2-isopropylprop-2-enyl-, 1-isopropylprop-2-enyl-, (E)-2-propylprop-1-enyl-, (Z)-2-propylprop-1-enyl-, (E)-1-propylprop-1-enyl-, (Z)-1-propylprop-1-enyl, (E)-2-isopropylprop-1-enyl-, (Z)-2-isopropylprop-1-enyl-, (E)-1-isopropyl prop-1-enyl-, (Z)-1-isopropylprop-1-enyl-, (E)-3,3-dimethylprop-1-enyl-, (Z)-3,3-dimethylprop-1-enyl-, 1-(1,1-dimethylethyl)-ethenyl.

A vinyl or allyl radical is preferred.

$C_n$-Alkynyl:

Monovalent, straight-chain or branched hydrocarbon radical having n carbon atoms and at least one triple bond.

A $C_2$-$C_6$ alkynyl radical includes inter alia for example: ethynyl-, prop-1-ynyl-, prop-2-ynyl-, but-1-ynyl-, but-2-ynyl-, but-3-ynyl-, pent-1-ynyl-, prop-2-ynyl-, pent-3-ynyl-, pent-4-ynyl-, hexyl-1-ynyl-, hex-2-ynyl-, hex-3-ynyl-, hex-4-ynyl-, hex-5-ynyl-, 1-methylprop-2-ynyl-, 2-methylbut-3-ynyl-, 1-methylbut-3-ynyl, 1-methylbut-2-ynyl-, 3-methylbut-1-ynyl-, 1-ethylprop-2-ynyl-, 3-methylpent-4-ynyl, 2-methylpent-4-ynyl-, 1-methylpent-4-ynyl-, 2-methylpent-3-ynyl-, 1-methylpent-3-ynyl-, 4-methylpent-2-ynyl-, 1-methylpent-2-ynyl-, 4-methylpent-1-ynyl-, 3-methylpent-1-ynyl-, 2-ethylbut-3-ynyl-, 1-ethylbut-3-ynyl-, 1-ethylbut-2-ynyl-, 1-propylprop-2-ynyl-, 1-isopropylprop-2-ynyl-, 2,2-dimethylbut-3-ynyl-, 1,1-dimethylbut-3-ynyl-, 1,1-dimethylbut-2-ynyl- or a 3,3-dimethylbut-1-ynyl-.

An ethynyl, prop-1-ynyl or prop-2-ynyl radical is preferred.

$C_n$-Cycloalkyl:

Monovalent, cyclic hydrocarbon ring having n carbon atoms.

$C_3$-$C_7$-Cycloalkyl ring includes:

cyclopropyl, cyclobutyl, cyclopentyl or cyclohexyl and cycloheptyl.

A cyclopropyl, cyclobutyl, cyclopentyl or a cyclohexyl ring is preferred.

$C_n$-Alkoxy:

Straight-chain or branched $C_n$-alkyl ether residue of the formula —OR with R=alkyl.

$C_n$-Fluoroalkoxy:

Straight-chain or branched $C_n$-fluoroalkyl ether residue of the formula —OR with R=$C_n$-fluoroalkyl.

$C_n$-Aryl $C_n$-Aryl is a monovalent, aromatic ring system without heteroatom having n hydrocarbon atoms.

$C_6$-Aryl is phenyl. $C_{10}$-Aryl is naphthyl.

Phenyl is preferred.

Heteroatoms

Heteroatoms mean oxygen, nitrogen or sulphur atoms.

Heteroaryl

Heteroaryl is a monovalent, aromatic ring system having at least one heteroatom different from a carbon. Heteroatoms which may be present are nitrogen atoms, oxygen atoms and/or sulphur atoms. The valence bonds may be on any aromatic carbon atom or on a nitrogen atom.

A monocyclic heteroaryl ring according to the present invention has 5 or 6 ring atoms.

Heteroaryl rings having 5 ring atoms include for example the rings: thienyl, thiazolyl, furanyl, pyrrolyl, oxazolyl, imidazolyl, pyrazolyl, isoxazolyl, isothiazolyl, oxadiazolyl, triazolyl, tetrazolyl and thiadiazolyl.

Heteroaryl rings having 6 ring atoms include for example the rings: pyridinyl, pyridazinyl, pyrimidinyl, pyrazinyl and triazinyl.

A bicyclic heteroaryl ring according to the present invention has 9 to 10 ring atoms.

Heteroaryl rings having 9 ring atoms include for example the rings: indolyl, isoindolyl, indazolyl, benzothiazolyl, benzofuranyl, benzothiophenyl, benzimidazolyl, benzoxazolyl, azocinyl, indolizinyl, purinyl.

Heteroaryl rings having 10 ring atoms include for example the rings: isoquinolinyl, quinolinyl, cinnolinyl, quinazolinyl, quioxalinyl, phthalazinyl, 1,7- or 1,8-naphthyridinyl, pteridinyl.

Monocyclic heteroaryl rings having 5 or 6 ring atoms are preferred.

Hydrogenated bicyclic aryl or heteroaryl rings are bicyclic compounds in which one ring is in partly or completely hydrogenated form. The valence bond may be on any atom of the aromatic part of the hydrogenated bicyclic aryl or heteroaryl ring.

Hydrogenated bicyclic aryl or heteroaryl rings include for example the rings: indanyl, 1,2,3,4-tetrahydronaphthalenyl, 1,2,3,4-tetrahydroisoquinolinyl, 1,2,3,4-tetrahydroquinolinyl, 2,3-dihydro-1H-indolyl, 2,3-dihydro-1H-isoindolyl, 4,5,6,7-tetrahydrothieno[2,3-c]pyridinyl, 4,5,6,7-tetrahydrothieno[3,2-c]pyridinyl, 2,3-dihydrobenzofuranyl, benzo[1,3]dioxolyl, 2,3-dihydrobenzo[1,4]dioxinyl, chromanyl, 1,2,3,4-tetrahydroquinoxalinyl, 3,4-dihydro-2H-benzo[1,4]oxazinyl.

Hydrogenated bicyclic aryl or heteroaryl rings in which one ring is in partly or completely hydrogenated form may optionally comprise one or two carbonyl groups in the ring system.

Examples thereof are indolonyl, isoindolonyl, benzoxazinonyl, phthalazinonyl, quinolonyl, isoquinolonyl, phthalidyl, thiophthalidyl.

Heterocyclyl

Heterocyclyl in the context of the invention is a completely hydrogenated heteroaryl (completed hydrogenated heteroaryl=saturated heterocyclyl), i.e. a nonaromatic ring system having at least one heteroatom different from a carbon. Heteroatoms which may occur are nitrogen atoms, oxygen atoms and/or sulphur atoms. The valence bond may be on any carbon atom or on a nitrogen atom.

Heterocyclyl ring having 3 ring atoms includes for example: aziridinyl.

Heterocyclyl ring having 4 ring atoms includes for example: azetidinyl, oxetanyl.

Heterocyclyl rings having 5 ring atoms include for example the rings: pyrrolidinyl, imidazolidinyl, pyrazolidinyl and tetrahydrofuranyl.

Heterocyclyl rings having 6 ring atoms include for example the rings: piperidinyl, piperazinyl, morpholinyl, tetrahydropyranyl and thiomorpholinyl Heterocyclyl rings having 7 ring atoms include for example the rings: azepanyl, oxepanyl, [1,3]-diazepanyl, [1,4]-diazepanyl.

Heterocyclyl rings having 8 ring atoms include for example: oxocanyl, azocanyl.

Heterocyclyl rings may optionally be partly unsaturated and/or also comprise a carbonyl group in the ring.

Examples thereof are dihydrofuran-2-onyl, pyrrolidin-2-onyl, piperazin-2-onyl, morpholin-2-onyl, 3(2H)-pyridazinonyl, 5,6-dihydro-2-pyran-2-onyl, 5,6-dihydropyridin-2(1H)-onyl, 2-piperidonyl, 1,2,3,6-tetrahydropyridinyl.

Halogen

The term halogen includes fluorine, chlorine, bromine and iodine.

Likewise to be regarded as encompassed by the present invention are all compounds which result from every possible combination of the abovementioned possible, preferred and particularly preferred meanings of the substituents.

Special embodiments of the invention moreover consist of compounds which result from combination of the meanings disclosed for the substituents directly in the examples.

Likewise to be regarded as encompassed by the present invention are the salts of the compounds.

Formulation of the compounds according to the invention to give pharmaceutical products takes place in a manner known per se by converting the active ingredient(s) with the excipients customary in pharmaceutical technology into the desired administration form.

Excipients which can be employed in this connection are, for example, carrier substances, fillers, disintegrants, binders, humectants, lubricants, absorbents and adsorbents, diluents, solvents, cosolvents, emulsifiers, solubilizers, masking flavours, colorants, preservatives, stabilizers, wetting agents, salts to alter the osmotic pressure or buffers. Reference should be made in this connection to Remington's Pharmaceutical Science, 15th ed. Mack Publishing Company, East Pennsylvania (1980).

The pharmaceutical formulations may be
in solid form, for example as tablets, coated tablets, pills, suppositories, capsules, transdermal systems or
in semisolid form, for example as ointments, creams, gels, suppositories, emulsions or
in liquid form, for example as solutions, tinctures, suspensions or emulsions.

Excipients in the context of the invention may be, for example, salts, saccharides (mono-, di-, tri-, oligo-, and/or polysaccharides), proteins, amino acids, peptides, fats, waxes, oils, hydrocarbons and derivatives thereof, where the excipients may be of natural origin or may be obtained by synthesis or partial synthesis.

Suitable for oral or peroral administration are in particular tablets, coated tablets, capsules, pills, powders, granules, pastilles, suspensions, emulsions or solutions. Suitable for parenteral administration are in particular suspensions, emulsions and especially solutions.

Owing to their antiinflammatory and additional immunosuppressant effect, the compounds of the invention of the general formula (I) can be used as medicaments for the treatment or prophylaxis of the following pathological states in mammals and humans, for local and systemic administration:

(i) pulmonary disorders associated with inflammatory, allergic and/or proliferative processes:
   chronic obstructive pulmonary disorders of any origin, especially bronchial asthma
   bronchitis of varying origin
   adult respiratory distress syndrome (ARDS), acute respiratory distress syndrome
   bronchiectases
   all types of restrictive pulmonary disorders, especially allergic alveolitis,
   pulmonary oedema, especially allergic
   sarcoidoses and granulomatoses, especially Boeck's disease (ii) rheumatic disorders/autoimmune diseases/joint disorders associated with inflammatory, allergic and/or proliferative processes:
   all types of rheumatic disorders, especially rheumatoid arthritis, acute rheumatic fever, polymyalgia rheumatica, Behcet's disease
   reactive arthritis
   inflammatory soft tissue disorders of other origin
   arthritic symptoms associated with degenerative joint disorders (arthroses)
   collagenoses of any origin, e.g. systemic lupus erythematosus,
   scleroderma, polymyositis, dermatomyositis, Sjögren's syndrome, Still's syndrome, Felty's syndrome
   sarcoidoses and granulomatoses
   soft tissue rheumatism (iii) allergies or pseudoallergic disorders associated with inflammatory and/or proliferative processes:
   all types of allergic reactions, e.g. angioedema, hay fever, insect bite, allergic reactions to drugs, blood derivatives, contrast media etc., anaphylactic shock, urticaria, allergic and irritative contact dermatitis, allergic vascular disorders
   allergic vasculitis (iv) vessel inflammations (vasculitides)
   panarteritis nodosa, temporal arteritis, erythema nodosum
   polyarteritis nodosa
   Wegner's granulomatosis
   giant cell arteritis (v) dermatological disorders associated with inflammatory, allergic and/or proliferative processes:
   atopic dermatitis (especially in children)
   all types of eczema such as, for example, atopic eczema (especially in children)
   exanthemas of any origin or dermatoses
   psoriasis and parapsoriasis group
   pityriasis rubra pilaris
   erythematous disorders induced by various noxae, e.g. radiation, chemicals, burns etc.
   bullous dermatoses such as, for example, autoimmune pemphigus vulgaris, bullous pemphigoid
   lichenoid disorders
   pruritus (e.g. of allergic origin)
   rosacea group
   erythema exudativum multiforme
   manifestation of vascular disorders
   hair loss such as alopecia areata
   cutaneous lymphomas (vi) renal disorders associated with inflammatory, allergic and/or proliferative processes:
   nephrotic syndrome
   all nephritides, e.g. glomerulonephritis (vii) hepatic disorders associated with inflammatory, allergic and/or proliferative processes:
   acute hepatitis of varying origin
   chronic aggressive and/or chronic intermittent hepatitis (viii) gastrointestinal disorders associated with inflammatory, allergic and/or proliferative processes:
   regional enteritis (Crohn's disease)
   ulcerative colitis
   gastroenteritides of other origin, e.g. indigenous sprue (ix) ocular disorders associated with inflammatory, allergic and/or proliferative processes:
   allergic keratitis, uveitis, iritis,
   conjunctivitis
   blepharitis
   optic neuritis
   chorioiditis
   sympathetic ophthalmia (x) ear-nose-throat disorders associated with inflammatory, allergic and/or proliferative processes:
   allergic rhinitis, hay fever
   otitis externa, e.g. caused by contact eczema (xi) neurological disorders associated with inflammatory, allergic and/or proliferative processes:
cerebral oedema, especially allergic cerebral oedema
multiple sclerosis
acute encephalomyelitis
meningitis, especially allergic
Guillain-Barre syndrome
Alzheimer's disease
(xii) haematological disorders associated with inflammatory, allergic and/or proliferative processes such as, for example, Hodgkin's disease or non-Hodgkin lymphomas, thrombocytaemias, erythrocytoses
acquired haemolytic anaemia
idiopathic thrombocytopenia
idiopathic granulocytopenia
(xiii) neoplastic disorders associated with inflammatory, allergic and/or proliferative processes
acute lymphatic leukaemia
malignant lymphomas
lymphogranulomatoses
lymphosarcomas
(xiv) endocrine disorders associated with inflammatory, allergic and/or proliferative processes such as, for example:
endocrine orbitopathy
de Quervain thyroiditis
Hashimoto thyroiditis
Basedow's disease
granulomatous thyroiditis
lymphadenoid goitre
autoimmune adrenalitis
diabetes mellitus, especially type 1 diabetes
endometriosis
(xv) organ and tissue transplantations, graft-versus-host disease
(xvi) severe states of shock, e.g. anaphylactic shock, systemic inflammatory response syndrome (SIRS)

One aspect of the invention is the use of the compounds according to the invention of the general formula (I) for manufacturing a pharmaceutical.

A further aspect of the invention is the use of the compounds according to the invention for the treatment of disorders associated with inflammatory, allergic and/or proliferative processes.

In the general formula (I), $Q_1$ may be a heteroaryl ring having 5 ring atoms.

$Q_1$ is preferably a pyrazolyl, thienyl, imidazolyl or 1,2,4-oxadiazolyl ring.

$Q_1$ is particularly preferably a pyrazolyl or thienyl ring.

In the general formula (I), $R^1$ and $R^2$ may be independently of one another:
(i) hydrogen, hydroxy, nitro, halogen, cyano, —$CF_3$, —$NR^5R^6$ or
(ii) $C(O)$—$R^{10}$, —$C(O)$—$R^7$, —$C(O)$—$C_1$-$C_3$-fluoroalkyl, —$C(O)$—$NR^5R^6$, —NH—$C(O)$—$R^7$ or
(iii) a $C_1$-$C_6$-alkyl, $C_2$-$C_6$-alkenyl, $C_2$-$C_6$-alkynyl, $C_1$-$C_6$-alkoxy, $C_1$-$C_6$-fluoroalkyl or a $C_1$-$C_6$-fluoroalkoxy radical, in each case optionally substituted one or more times, identically or differently, by —$C_1$-$C_3$-alkoxy, hydroxy, —$C(O)$—$R^{10}$ or —$NR^8R^9$, or
(iv) —O—$SO_2$—$NR^5R^6$, —$SO_2$—$R^7$, —$SO_2$—$NR^5R^6$.

$R^1$ and $R^2$ are preferably independently of one another:
(i) hydrogen, hydroxy, halogen, cyano, —$CF_3$, —$NR^5R^6$ or
(ii) a $C_1$-$C_6$-alkyl, $C_1$-$C_6$-alkoxy, $C_1$-$C_6$-fluoroalkyl or a $C_1$-$C_6$-fluoroalkoxy radical or
(iii) —$SO_2$—$R^7$.

$R^1$ and $R^2$ are particularly preferably independently of one another:
(i) hydrogen or
(ii) a $C_1$-$C_6$-alkyl radical.

In the general formula (I), $Q_2$ may be an aryl, heteroaryl or a hydrogenated bicyclic heteroaryl ring.

$Q_2$ is preferably a:
phenyl, thienyl, thiazolyl, furanyl, pyrrolyl, oxazolyl, imidazolyl, pyrazolyl, isoxazolyl, isothiazolyl, 1,2,3-triazolyl, pyridinyl, pyridazinyl, pyrimidinyl, pyrazinyl, 1,2,3,4-tetrahydroisoquinolinyl, 1,2,3,4-tetrahydroquinolinyl, 2,3-dihydro-1H-indolyl, 2,3-dihydro-1H-isoindolyl, 4,5,6,7-tetrahydrothieno[2,3-c]pyridinyl, 4,5,6,7-tetrahydrothieno[3,2-c]pyridinyl, 2,3-dihydrobenzofuranyl, benzo[1,3]dioxolyl, 2,3-dihydrobenzo[1,4]dioxinyl, 1,2,3,4-tetrahydroquinoxalinyl or a 3,4-dihydro-2H-benzo[1,4]oxazinyl ring.

$Q_2$ is particularly preferably a phenyl or pyrazolyl ring.

In the general formula (I), $R^3$ and $R^4$ may be independently of one another:
(i) hydrogen, halogen or —$NR^{11}R^{12}$, or
(ii) a $C_1$-$C_6$-alkyl or $C_1$-$C_6$-alkoxy radical which are optionally substituted in each case one or more times, identically or differently, by hydroxy, $C_1$-$C_3$-alkoxy, —$NR^8R^9$ or heterocyclyl, where the heterocyclyl ring may be substituted one or more times, identically or differently, by $C_1$-$C_3$-alkyl or —$C(O)$—$R^7$.

$R^3$ and $R^4$ are preferably independently of one another:
(i) hydrogen, halogen, —$NR^{11}R^{12}$ or
(ii) a $C_1$-$C_6$-alkyl or $C_1$-$C_6$-alkoxy radical, in each case optionally substituted by morpholine or —$NR^8R^9$.

$R^3$ and $R^4$ are particularly preferably independently of one another hydrogen or $C_1$-$C_6$-alkyl.

In the general formula (I), $R^5$ and $R^6$ can be independently of one another: hydrogen or a $C_1$-$C_6$-alkyl radical which is optionally substituted one or more times, identically or differently, by hydroxy, —$C_1$-$C_3$-alkoxy, —$NR^8R^9$ or heterocyclyl, where the heterocyclyl ring may be substituted one or more times, identically or differently, by $C_1$-$C_3$-alkyl or —$C(O)$—$R^7$, or $R^5$ and $R^6$ form alternatively together with the nitrogen atom a 5- to 7-membered ring which optionally comprises a further heteroatom in addition to the nitrogen atom and which is optionally substituted one or more times, identically or differently, by $C_1$-$C_6$-alkyl and/or by —$C(O)$—$R^7$.

$R^5$ and $R^6$ are preferably independently of one another hydrogen or a $C_1$-$C_6$-alkyl radical which may optionally be substituted one or more times, identically or differently, by hydroxy, —$NR^8R^9$, halogen or $C_1$-$C_3$-alkoxy.

$R^5$ and $R^6$ are particularly preferably independently of one another hydrogen or a $C_1$-$C_4$-alkyl radical.

In the general formula (I), $R^7$ may be a $C_1$-$C_6$-alkyl radical.

$R^7$ is preferably a $C_1$-$C_4$-alkyl radical.

$R^7$ is particularly preferably a $C_1$-$C_3$-alkyl radical.

In the general formula (I), $R^8$, $R^9$, $R^{10}$ may be independently of one another hydrogen or a $C_1$-$C_6$-alkyl radical.

It is preferred for $R^8$ and $R^9$ to be independently of one another hydrogen or a $C_1$-$C_4$-alkyl radical and for $R^{10}$ to be hydrogen.

It is particularly preferred for $R^8$ and $R^9$ to be independently of one another hydrogen or a $C_1$-$C_3$-alkyl radical and for $R^{10}$ to be hydrogen.

In the general formula (I), $R^{11}$ and $R^{12}$ may be independently of one another:
hydrogen or a $C_1$-$C_6$-alkyl radical which is optionally substituted one or more times, identically or differently, by hydroxy, —$C_1$-$C_3$-alkoxy, —$NR^8R^9$ or heterocyclyl, where the heterocyclyl ring may be substituted one or more times, identically or differently, by $C_1$-$C_3$-alkyl or —$C(O)$—$R^7$.

$R^{11}$ and $R^{12}$ are preferably independently of one another hydrogen or a $C_1$-$C_6$-alkyl radical which may optionally be substituted one or more times, identically or differently, by morpholine or by —N(CH$_3$)$_2$, —NH—CH$_3$ or —NH—C$_2$H$_5$.

A preferred subgroup is formed by compounds of the formula (I) with building blocks A, B, C and D,
in which the building blocks B and D are in ortho position relative to one another and $Q_1$ is a pyrazolyl, thienyl, imidazolyl or 1,2,4-oxadiazolyl ring, $R^1$ and $R^2$ are independently of one another
  (i) hydrogen, hydroxy, halogen, cyano, —CF$_3$, —NR$^5$R$^6$ or
  (ii) a $C_1$-$C_6$-alkyl, $C_1$-$C_6$-alkoxy, $C_1$-$C_6$-fluoroalkyl or a $C_1$-$C_6$-fluoroalkoxy radical or
  (iii) —SO$_2$R$^7$, $Q_2$ is a phenyl, thienyl, thiazolyl, furanyl, pyrrolyl, oxazolyl, imidazolyl, pyrazolyl, isoxazolyl, isothiazolyl, 1,2,3-triazolyl, pyridinyl, pyridazinyl, pyrimidinyl, pyrazinyl, 1,2,3,4-tetrahydroisoquinolinyl, 1,2,3,4-tetrahydroquinolinyl, 2,3-dihydro-1H-indolyl, 2,3-dihydro-1H-isoindolyl, 4,5,6,7-tetrahydrothieno[2,3-c]pyridinyl, 4,5,6,7-tetrahydrothieno[3,2-c]pyridinyl, 2,3-dihydrobenzofuranyl, benzo[1,3]dioxolyl, 2,3-dihydrobenzo[1,4]dioxinyl, 1,2,3,4-tetrahydroquinoxalinyl or a 3,4-dihydro-2H-benzo[1,4]oxazinyl ring, $R^3$ and $R^4$ are independently of one another
  (i) hydrogen, halogen, —NR$^{11}$R$^{12}$ or
  (ii) a $C_1$-$C_6$-alkyl or $C_1$-$C_6$-alkoxy radical,
  in each case optionally substituted by morpholine or —NR$^8$R$^9$,
where
  $R^5$ and $R^6$ are independently of one another hydrogen or a $C_1$-$C_6$ alkyl radical which may optionally be substituted one or more times, identically or differently, by hydroxy, —NR$^8$R$^9$, halogen or $C_1$-$C_3$-alkoxy, and
  $R^7$ is a $C_1$-$C_4$ alkyl radical, and
  $R^8$ and $R^9$ are independently of one another hydrogen or a $C_1$-$C_4$ alkyl radical,
  $R^{11}$ and $R^{12}$ are independently of one another hydrogen or a $C_1$-$C_6$ alkyl radical which may optionally be substituted one or more times, identically or differently, by morpholine or by —N(CH$_3$)$_2$, —NH—CH$_3$ or —NH—C$_2$H$_5$,
and the salts, enantiomers and diastereomers thereof.

Particular preference is given to compounds of the general formula (I) with building blocks A, B, C and D,
in which
the building blocks B and D are in ortho position relative to one another, and
$Q_1$ is a pyrazolyl or thienyl ring, and
$R^1$ and $R^2$ are independently of one another
  (i) hydrogen
  (ii) a $C_1$-$C_6$-alkyl radical
$Q_2$ is a phenyl or pyrazolyl ring, and
$R^3$ and $R^4$ are independently of one another hydrogen or a $C_1$-$C_6$-alkyl,
and the salts, enantiomers and diastereomers thereof.

Preparation of the Compounds According to the Invention
a) Preparation of Intermediates of the Formula (III)

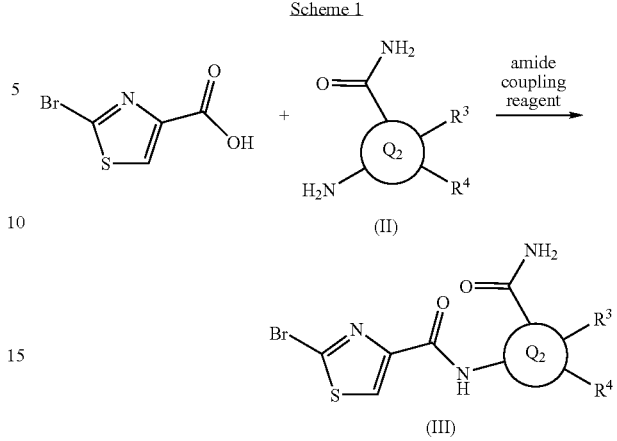

Scheme 1

2-Bromothiazole-4-carboxylic acid is reacted with intermediates of the formula (II) through an amide coupling reagent (see Sigma-Aldrich publication Chemfiles, Peptide Synthesis, 2007, 7, No. 2) to give intermediates of the formula (III). It is possible in this case to use for example carbodiimides (for example N-cyclohexyl-N'-(2-morpholinoethyl)carbodiimide metho-p-toluenesulphonate CAS2491-17-0) or uronium salts (for example O-(7-azabenzotriazol-1-yl)-N,N,N',N'-tetramethyluronium hexafluorophosphate (HATU)) in combination with a base such as, for example, pyridine.

b) Preparation of the Final Product

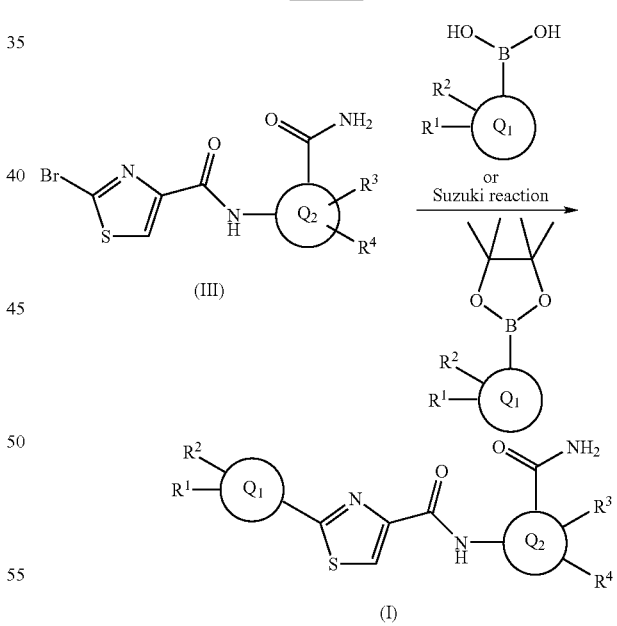

Scheme 2

Intermediates of the formula (III) are reacted with boronic acids or boronic acid pinacol esters in a Suzuki-Miyaura reaction to give the compounds according to the invention of the formula (I). Suitable catalysts or ligands in this case are for example the catalysts or catalyst systems described in N. Miyaura, A. Suzuki, *Chem. Rev.*; 1995; 95(7); 2457-2483 or in C. J. O'Brien et al. *Chem. Eur. J.* 2006, 12, 4743-4748 and in the Sigma-Aldrich publication *Chemfiles, Catalysis* 2007, 7, No. 5.

In this case, $Q_1$, $Q_2$, $R^1$, $R^2$, $R^3$ and $R^4$ have the meanings indicated in general formula (I) according to Claims 1 to 7.

Purification of the Compounds According to the Invention

In some cases, the compounds according to the invention can be purified by preparative HPLC, for example by an autopurifier apparatus from Waters (detection of the compounds by UV detection and electrospray ionization) in combination with commercially available, prepacked HPLC columns (for example XBridge column (from Waters), C18, 5 μm, 30×100 mm). Acetonitrile/water+0.1% trifluoroacetic acid can be used as solvent system (flow rate 50 ml/min). The HPLC solvent mixture can be removed by freeze-drying or centrifugation. The compounds obtained in this way may be in the form of trifluoroacetic acid (TFA) salts and can be converted into the respective free bases by standard laboratory procedures known to the skilled person. In some cases, the compounds according to the invention can be purified by chromatography on silica gel. In this case for example prepacked silica gel cartridges (for example Isolute® Flash silica gel from Separtis) in combination with a Flashmaster II chromatography apparatus (Argonaut/Biotage) and chromatography solvent or mixtures thereof such as, for example, hexane, ethyl acetate, and dichloromethane and methanol, can be considered.

Structural Analysis of the Compounds According to the Invention:

In some cases, the compounds according to the invention are analysed by LC-MS: retention times $R_t$ from the LC-MS analysis: detection: UV=200-400 nm (Acquity HPLC system from Waters)/MS 100-800 daltons; 20 V (Micromass/Waters ZQ 4000) in ESI$^+$ mode (to generate positively charged molecular ions); HPLC column: XBridge (Waters), 2.1×50 mm, BEH 1.7 μm; eluents: A: $H_2O$/0.05% HC(O)OH, B: CH3CN/0.05% HC(O)OH. Gradient: 10-90% B in 1.7 min, 90% B for 0.2 min, 98-2% B in 0.6 min; flow rate: 1.3 ml/min. The statement LC-MS (ZQ) refers to the use of a Waters ZQ4000 apparatus and the statement LC-MS (SQD) refers to the use of a Single Quadrupol API (Atomic Pressure Ionization) mass detector (Waters) to record a mass spectrum.

EXAMPLE 1

2-(1H-Pyrazol-4-yl)thiazole-4-(3-carbamoyl-1-methyl-1H-pyrazol-4-yl)-carboxamide

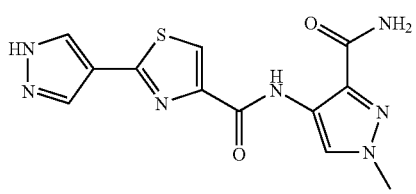

a) Preparation of Intermediate III.1

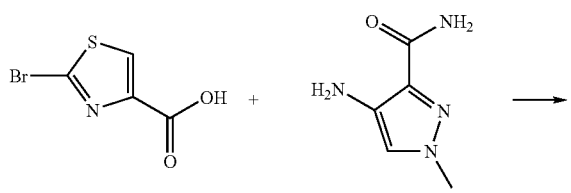

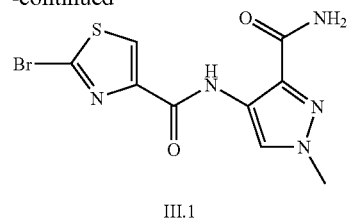

III.1

A mixture of 2-bromothiazole-4-carboxylic acid (891 mg), 4-amino-1-methyl-1H-pyrazole-3-carboxamide (600 mg) and HATU (1.95 g) in DMF (5 ml) and ethyldiisopropylamine (1.5 ml) is stirred at room temperature for 20 h and then poured into ice-water. The precipitated solid is filtered off, washed twice with water and three times each with diethyl ether and ethyl acetate and dried in vacuo (889 mg).

$C_9H_8BrN_5O_2S$ (329.0), LC-MS (ZQ): $R_t$=0.87, m/z=330 [M+H]$^+$. 1H-NMR (300 MHz, D6-DMSO): 3.88 (s, 3H), 7.45 (br. s., 1H), 7.70 (br. s., 1H), 8.31 (s, 1H), 8.41 (s, 1H), 11.0 (s, 1H).

b) Preparation of the Final Product

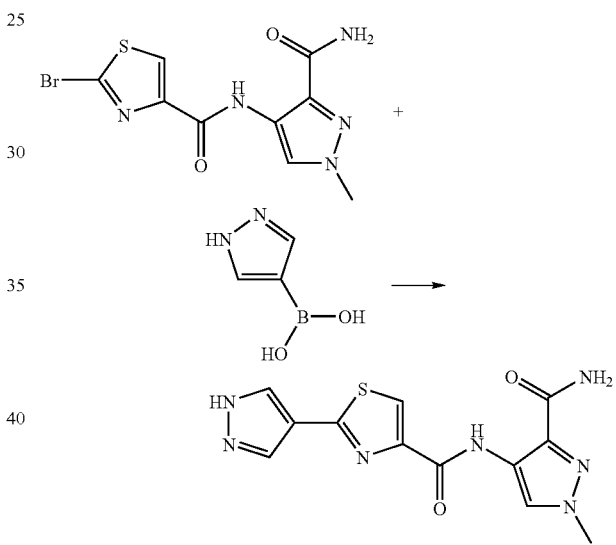

Intermediate III.1 (150 mg) and 1H-pyrazole-4-boronic acid (152 mg) are mixed with THF (3 ml) and potassium carbonate solution (aqueous, 1M, 2 ml) and then 1,1'-bis (diphenylphosphino)ferrocenepalladium dichloride-dichloromethane complex (74 mg) is added, and the mixture is heated in a microwave at 130° C. for 45 min (CEM Explorer apparatus from CEM, 300 watts). An aqueous working up with ethyl acetate and water is carried out, the organic phase is dried with sodium sulphate and concentrated, and the residue is purified by HPLC. 4.5 mg of a white foam are obtained.

Conditions for the Preparative Purification:

| Column: | XBridge (from Waters) C18 5 μ, 150 × 30 mm | | |
|---|---|---|---|
| Solvent A: | H2O/0.1% HC(O)OH | | |
| Solvent B: | acetonitrile | | |
| Gradient: | 0 min | 90% A | 10% B |
| | 1.00 min | 90% A | 10% B |
| | 7.50 min | 60% A | 40% B |
| | 7.52 min | 1% A | 99% B |
| | 10.00 min | 1% A | 99% B |

-continued

| | |
|---|---|
| Flow rate: | 50.0 ml/min |
| Volume injected: | 1 × 1.5 ml |
| Detection: | DAD (200-400 nm) TAC; MS-ESI+ (m/z = 160-1000 m/z) TIC |
| Temperature: | room temperature. |

Conditions for the HPLC Analysis:

| | | | |
|---|---|---|---|
| Column: | Acquity BEH C18 1.7 µm 50 × 2.1 mm | | |
| Solvent A: | H2O/0.05% HC(O)OH | | |
| Solvent B: | acetonitrile | | |
| Gradient: | 0 min | 99% A | 1% B |
| | 1.6 min | 1% A | 99% B |
| | 2.0 min | 1% A | 99% B |
| Flow rate: | 0.8 ml/min | | |
| Volume injected: | 2.0 µl | | |
| Detection: | DAD (200-400 nm) TAC; MS-ESI+, ESI− (120-1000 m/z) TIC | | |
| Temperature: | 60° C. | | |

$C_{12}H_{11}N_7O_2S$ (317.3), $R_t$=0.71, m/z=318.2 [M+H]$^+$.

EXAMPLE 2

N-[2-(Aminocarbonyl)phenyl]-2-(5-methyl-3-thienyl)-4-thiazole-carboxamide

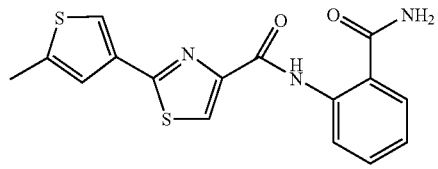

a) Preparation of intermediate III.2
N-[2-(Aminocarbonyl)phenyl]-2-bromo-4-thiazolecarboxamide

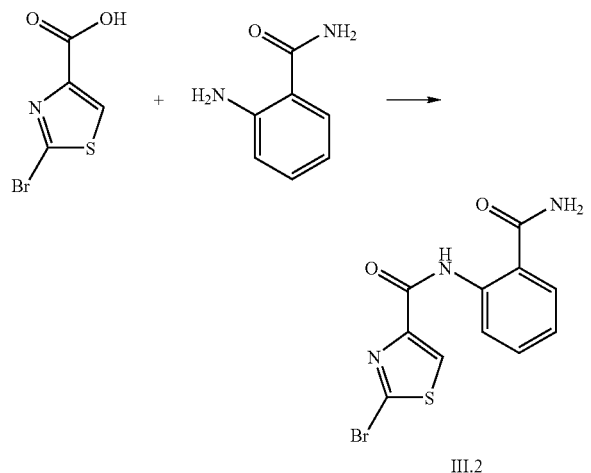

2-Bromo-4-thiazolecarboxylic acid (1 g), HATU (2.01 g) and 2-aminobenzamide (0.65 g) are introduced into N,N-dimethylformamide (DMF) (20 ml). The mixture is cooled with an ice bath, and N,N-diisopropylethylamine (0.90 ml) is added. The reaction mixture is stirred at room temperature for 6 days, poured into ice-water and allowed to thaw with stirring, and the precipitated solid is filtered off with suction, washed twice with water, twice with diethyl ether and dried in vacuo. Intermediate III.2 is obtained as a solid (1.4 g).

$C_{11}H_8BrN_3O_2S$, M=326.2. 1H-NMR (300 MHz, D6-DMSO): δ=7.20 (m, 1H), 7.56 (m, 1H), 7.79 (s, 1H), 7.84 (m, 1H), 8.30 (s, 1H), 8.47 (m, 1H), 8.67 (m, 1H), 12.9 (s, 1H).

b) Preparation of the Final Product
N-[2-(Aminocarbonyl)phenyl]-2-(5-methyl-3-thienyl)-4-thiazole-carboxamide is prepared using the Suzuki reaction (in analogy to A. Suzuki et al, *J. Am. chem. Soc.* 1989, 111, 314).

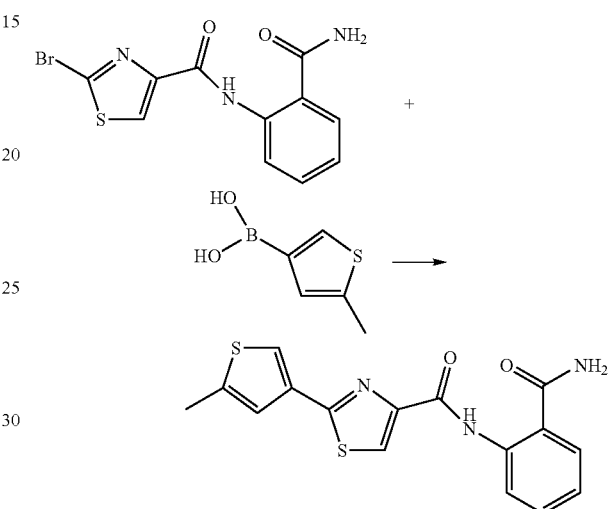

Intermediate III.2 (65 mg) and 2-methyl-4-thiopheneboronic acid (40 mg) are introduced into toluene (1.5 ml), ethanol (1.5 ml) and aqueous sodium carbonate solution (2M, 180 microlitres), Pd(PPh₃)₄ (23 mg) is added, and the mixture is heated at 120° C. (300 watts) in the microwave (CEM Explorer apparatus) for 15 min. The reaction mixture is diluted with water and extracted with ethyl acetate. The organic phase is concentrated and the residue is purified by HPLC. Example 1.3 (35 mg) is obtained as solid.

$C_{16}H_{13}N_3O_2S_2$, M=343.4, LC-MS (ZQ):$R_t$=1.20, m/z=344 [M+H]$^+$.

EXAMPLE 3

N-[2-(Aminocarbonyl)-5-methylphenyl]-2-(1H-pyrazol-4-yl)thiazole-4-carboxamide

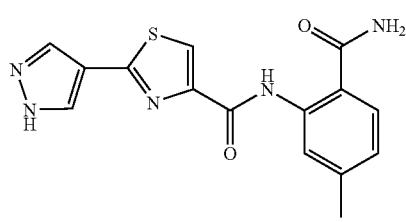

a) Preparation of Intermediate III.3
N-[2-(Aminocarbonyl)-5-methylphenyl]-2-bromo-4-thiazolecarboxamide

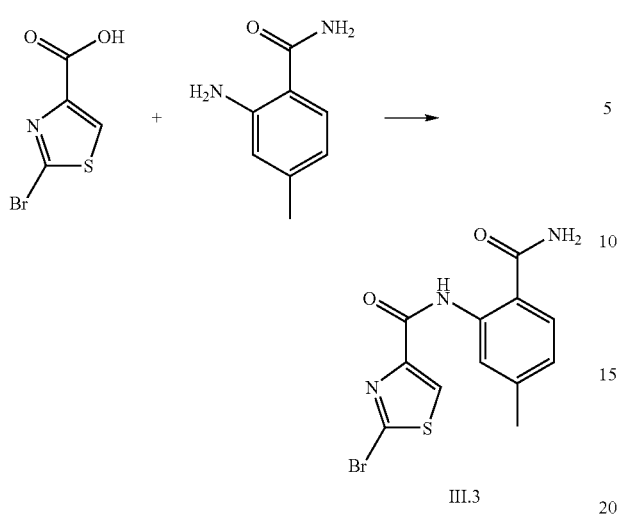

2-Bromo-4-thiazolecarboxylic acid and 2-amino-4-methylbenzamide are reacted in analogy to the synthesis of intermediate III.2 to give N-[2-(aminocarbonyl)-5-methylphenyl]-2-bromo-4-thiazolecarboxamide (intermediate III.3).

$C_{12}H_{10}BrN_3O_2S$, M=339.0, LC-MS (ZQ): $R_t$=1.04, m/z=340 [M+H]$^+$. 1H-NMR (300 MHz, D6-DMSO): δ=2.32 (s, 3H), 6.97 (m, 1H) 7.65 (br. s., 1H), 7.70 (d, 1H), 8.18 (br. s., 1H), 8.40 (s, 1H), 8.49 (m, 1H), 13.0 (s, 1H).

b) Preparation of the Final Product

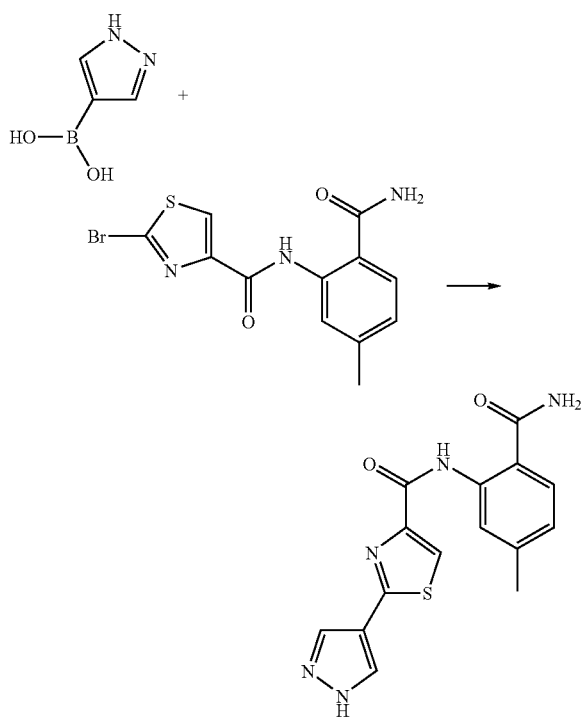

A mixture of intermediate III.3 (150 mg) 1H-pyrazole-4-boronic acid (63 mg) in ethylene glycol dimethyl ether (3 ml) and aqueous sodium bicarbonate solution (2 ml, 2M) is heated in a microwave (CEM Explorer, 300 watt) at 110° C. for 40 min in the presence of Pd(PPh$_3$)$_4$ (55 mg). Working up as in Example 2 results in N-[2-(aminocarbonyl)-5-methylphenyl]-2-(1H-pyrazol-4-yl)thiazole-4-carboxamide as a solid (4.9 mg).

$C_{15}H_{13}N_5O_2S$, M=327.1, LC-MS (ZQ): $R_t$=0.99, m/z=328 [M+H]$^+$.

TLR-Induced Cytokine Release in Human "Peripheral Blood Mononuclear Cells" (PBMC)

Test Principle

PBMCs isolated from human whole blood are stimulated using a TLR ligand.

The cytokine determination is carried out by means of ELISA kits; a proliferation/cell metabolism determination is carried out using Alamar Blue.

PBMC Isolation:

For the cell preparation, about 200 ml of blood are treated with an anticoagulant (e.g. citrate Monovettes). Per Leucosep tube, 15 ml of Histopaque (room temperature, RT) are poured in and forced downwards through the inserted frit by brief initial centrifugation (one minute at 1000×g, RT). 20 ml of blood are added to the tubes prepared in this way and centrifuged at 800×g for 15 minutes (RT). After centrifugation, the following layered arrangement results from the top to the bottom:

plasma-PBMC-Histopaque-filter disc-Histopaque-erythrocytes and granulocytes. The supernatant plasma is aspirated. The PBMC are transferred together with the underlying Histopaque to a new 50 ml tube, the contents of two Leucosep tubes always being added to one 50 ml tube. The 50 ml tubes are then filled to 50 ml with PBS. This cell suspension is centrifuged at 300×g (RT) for 10 minutes.

The liquid supernatant is tipped off and the cell pellet is resuspended with a little PBS and subsequently filled to 50 ml with PBS. This washing step is repeated twice. The resulting pellet is taken up in a defined volume of medium (with additives). For the testing of the substances, PBMC are incubated for 18 hours with titrated concentrations of the test substances, e.g. in the presence or absence of TLR7 or TLR9 ligands. On the next day, the supernatants are investigated for the content of TNF-alpha or other cytokines or chemokines by means of specific ELISA. The metabolic activity of the treated cells is determined with the aid of Alamar Blue.

Results:

| Example | EC$_{50}$ (TNF-α TLR7) |
|---|---|
| 1 | 5.0e−8 mol/L |
| 2 | 3.8e−6 mol/L |
| 3 | 1.2e−7 mol/L |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 07076070, filed Dec. 10, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A compound of the formula (I) with building blocks A, B, C and D

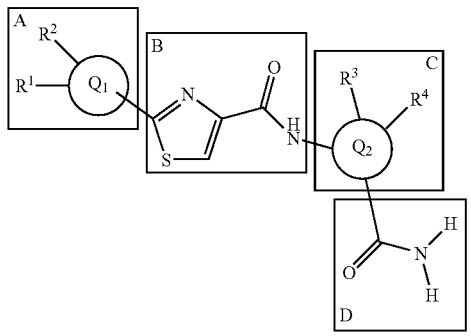

in which
the building blocks B and D are in ortho position relative to one another, and
$Q_1$ is a heteroaryl ring having 5 ring atoms,
$R^1$ and $R^2$ are independently of one another
(i) hydrogen, hydroxy, nitro, halogen, cyano, $-CF_3$, $-NR^5R^6$ or
(ii) $-C(O)-R^{10}$, $-C(O)-R^7$, $-C(O)-C_1-C_3$-fluoroalkyl, $-C(O)-NR^5R^6$, $-NH-C(O)-R^7$ or
(iii) a $C_1-C_6$-alkyl, $C_2-C_6$-alkenyl, $C_2-C_6$-alkynyl, $C_1-C_6$-alkoxy, $C_1-C_6$-fluoroalkyl or a $C_1-C_6$-fluoroalkoxy radical,
in each case optionally substituted one or more times, identically or differently, by $C_1-C_3$-alkoxy, hydroxy, $-C(O)-R^{10}$ or $-NR^8R^9$, or
(iv) $-O-SO_2$, $-NR^5R^6$, $-SO_2-R^7$, $-SO^2-NR^5R^6$
$Q_2$ is an aryl, heteroaryl or a hydrogenated bicyclic heteroaryl ring;
$R^3$ and $R^4$ are independently of one another
(i) hydrogen, halogen or $-NR^{11}R^{12}$, or
(ii) a $C_1-C_6$-alkyl or $C_1-C_6$-alkoxy radical which are in each case optionally substituted one or more times, identically or differently, by hydroxy, $C_1-C_3$-alkoxy, $-NR^8R^9$ or heterocyclyl, where the heterocyclyl ring may be substituted one or more times, identically or differently, by $C_1-C_3$-alkyl or $-C(O)-R^7$,
where
$R^5$ and $R^6$ are independently of one another hydrogen or a $C_1-C_6$-alkyl radical which is optionally substituted one or more times, identically or differently, by hydroxy, $-C_1-C_3$-alkoxy, $-NR^8R^9$ or heterocyclyl, where the heterocyclyl ring may be substituted one or more times, identically or differently, by $C_1-C_3$-alkyl or $-C(O)-R^7$, or
$R^5$ and $R^6$ form alternatively together with the nitrogen atom a 5- to 7-membered ring which optionally comprises a further heteroatom in addition to the nitrogen atom, and which is optionally substituted one or more times, identically or differently, by $C^1-C_6$-alkyl and/or by $-C(O)-R^7$, and
$R^7$ is a $C_1-C_6$-alkyl radical, and
$R^8$, $R^9$, $R^{10}$ are independently of one another hydrogen or a $C_1-C_6$-alkyl radical, and
$R^{11}$ and $R^{12}$ are independently of one another hydrogen or a $C_1-C_6$-alkyl radical which is optionally substituted one or more times, identically or differently, by hydroxy, $-C_1-C_3$-alkoxy, $-NR^8R^9$ or heterocyclyl, where the heterocyclyl ring may be substituted one or more times, identically or differently, by $C_1-C_3$-alkyl or $-C(O)-R^7$,
or a salt, enantiomer or diastereomer thereof.

2. The compound Compounds of formula (I) according to claim 1 with building blocks A, B, C and D,
in which
the building blocks B and D are in ortho position relative to one another, and
$Q_1$ is a pyrazolyl, thienyl, imidazolyl or 1,2,4-oxadiazolyl ring,
$R^1$ and $R^2$ are independently of one another
(i) hydrogen, hydroxy, halogen, cyano, $-CF_3$, $-NR^5R^6$ or
(ii) a $C_1-C_6$-alkyl, $C_1-C_6$-alkoxy, $C_1-C_6$-fluoroalkyl or a $C_1-C_6$-fluoroalkoxy radical or
(iii) $-SO_2R^7$,
$Q_2$ is a phenyl, thienyl, thiazolyl, furanyl, pyrrolyl, oxazolyl, imidazolyl, pyrazolyl, isoxazolyl, isothiazolyl, 1,2,3-triazolyl, pyridinyl, pyridazinyl, pyrimidinyl, pyrazinyl, 1,2,3,4-tetrahydroisoquinolinyl, 1,2,3,4-tetrahydroquinolinyl, 2,3-dihydro-1H-indolyl, 2,3-dihydro-1H-isoindolyl, 4,5,6,7-tetrahydrothieno[2,3-c]pyridinyl, 4,5,6,7-tetrahydrothieno[3,2-c]pyridinyl, 2,3-dihydrobenzofuranyl, benzo[1,3]dioxolyl, 2,3-dihydrobenzo[1,4]dioxinyl, 1,2,3,4-tetrahydroquinoxalinyl or a 3,4-dihydro-2H-benzo[1,4]oxazinyl ring,
$R^3$ and $R^4$ are independently of one another
(i) hydrogen, halogen, $-NR^{11}R^{12}$ or
(ii) a $C_1-C_6$-alkyl or $C_1-C_6$-alkoxy radical, in each case optionally substituted by morpholine or $-NR^8R^9$,
where
$R^5$ and $R^6$ are independently of one another hydrogen or a $C_1-C_6$ alkyl radical which may optionally be substituted one or more times, identically or differently, by hydroxy, $-NR^8R^9$ or $C_1-C_3$-alkoxy, and
$R^7$ is a $C_1-C_4$ alkyl radical, and
$R^8$ and $R^9$ are independently of one another hydrogen or a $C_1-C_4$ alkyl radical,
$R^{11}$ and $R^{12}$ are independently of one another hydrogen or a $C_1-C_6$ alkyl radical which may optionally be substituted one or more times, identically or differently, by morpholine or by $-N(CH_3)_2$, $-NH-CH_3$ or $-NH-C_2H_5$,
or a salt, enantiomer or and diastereomer thereof.

3. The compound of formula (I) with building blocks A, B, C and D according to claim 1,
in which
$Q_1$ is a pyrazolyl or thienyl ring,
or a salt, enantiomer or diastereomer thereof.

4. The compound of the general formula (I) with building blocks A, B, C and D according to claim 1, in which
$R^1$ and $R^2$ are independently of one another
(i) hydrogen, or
(ii) a $C_1-C_6$-alkyl radical,
or a salt, enantiomer or diastereomer thereof.

5. The compound of formula (I) with building blocks A, B, C and D according to claim 1,
in which
$Q_2$ is a phenyl or pyrazolyl ring,
or a salt, enantiomer and diastereomer thereof.

6. The compound of formula (I) with building blocks A, B, C and D according to claim 1,
in which
$R^3$ and $R^4$ are independently of one another hydrogen or $C_1$-$C_6$-alkyl, or a salt, enantiomer or diastereomer thereof.

7. The compound of formula (I) according to claim 1 with building blocks A, B, C and D
in which
the building blocks B and D are in ortho position relative to one another, and
$Q_1$ is a pyrazolyl or thienyl ring,
$R^1$ and $R^2$ are independently of one another
  (i) hydrogen
  (ii) a $C_1$-$C_6$-alkyl radical
$Q_2$ is a phenyl or pyrazolyl ring,
$R^3$ and $R^4$ are independently of one another hydrogen or $C_1$-$C_6$-alkyl,
or a salt, enantiomer or diastereomer thereof.

8. The compound according to claim 1, which is
2-(1H-pyrazol-4-yl)thiazole-4-(3-carbamoyl-1-methyl-1H-pyrazol-4-yl)carboxamide),
N-[2-(aminocarbonyl)phenyl]-2-(5-methyl-3-thienyl)-4-thiazolecarboxamide, or
N-[2-(aminocarbonyl)-5-methylphenyl]-2-(1H-pyrazol-4-yl)-thiazole-4-carboxamide.

9. A process for preparing a compound according to claim 1, comprising
a) reacting 2-bromothiazole-4-carboxylic acid with an intermediate of formula (II) with an amide coupling reagent

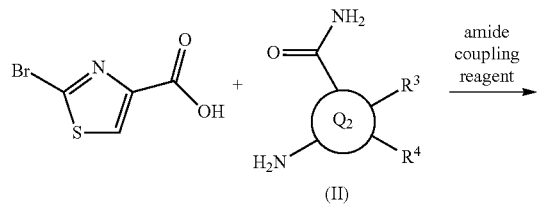

(II)

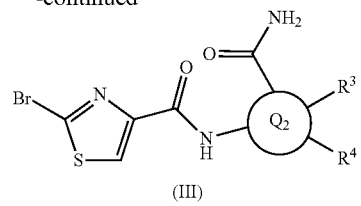

(III)

and
b) reaction of the intermediates of the formula (III) with boronic acids or boronic acid pinacol esters in a Suzuki-Miyaura reaction to give compounds of the formula (I)

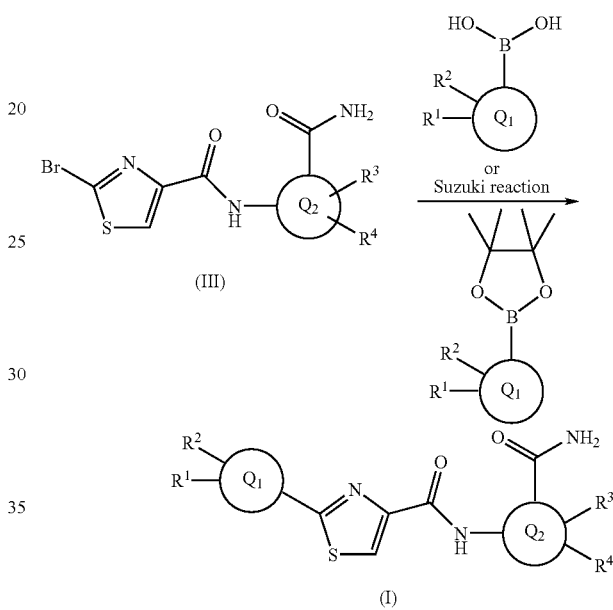

(I)

where
$Q_1$, $Q_2$, $R^1$, $R^2$, $R^3$ and $R^4$ have the meanings indicated in formula (I) according to claim 1.

10. A pharmaceutical composition comprising a compound according to claim 1, and a pharmaceutically acceptable carrier.

* * * * *